(12) United States Patent
Choi et al.

(10) Patent No.: US 11,951,678 B2
(45) Date of Patent: Apr. 9, 2024

(54) METHOD FOR MANUFACTURING FREESTANDING 3D PRINTING STRUCTURE

(71) Applicant: Korea Institute Of Materials Science, Changwon-si (KR)

(72) Inventors: Yeong-jin Choi, Changwon-si (KR); Hui-suk Yun, Changwon-si (KR); Hong-hyun Park, Changwon-si (KR)

(73) Assignee: KOREA INSTITUTE OF MATERIALS SCIENCE, Changwon-si (KR)

( * ) Notice: Subject to any disclaimer, the term of this patent is extended or adjusted under 35 U.S.C. 154(b) by 0 days.

(21) Appl. No.: 17/501,298

(22) Filed: Oct. 14, 2021

(65) Prior Publication Data

US 2022/0118686 A1 Apr. 21, 2022

(30) Foreign Application Priority Data

Oct. 15, 2020 (KR) .................. 10-2020-0133375

(51) Int. Cl.
*A61L 27/52* (2006.01)
*A61L 27/38* (2006.01)
*B29C 64/124* (2017.01)
*B33Y 10/00* (2015.01)
(Continued)

(52) U.S. Cl.
CPC ............ *B29C 64/124* (2017.08); *A61L 27/38* (2013.01); *A61L 27/52* (2013.01); *B33Y 10/00* (2014.12); *B33Y 70/10* (2020.01); *B33Y 80/00* (2014.12)

(58) Field of Classification Search
CPC .................. A61L 27/52; A61L 27/38
See application file for complete search history.

(56) References Cited

U.S. PATENT DOCUMENTS

| 10,150,258 | B2 * | 12/2018 | Feinberg | ................. B29C 64/40 |
| 11,192,292 | B2 * | 12/2021 | Fernandez-Nieves | ...................... B33Y 70/00 |
| 11,413,688 | B2 * | 8/2022 | Song | ..................... B33Y 10/00 |

(Continued)

FOREIGN PATENT DOCUMENTS

| KR | 20150028976 A | 3/2015 |
| KR | 10-1562556 B | 10/2015 |

(Continued)

OTHER PUBLICATIONS

Korean Notice of Allowance dated Nov. 29, 2022 for corresponding KR Patent Application No. 10-2020-0133375.

(Continued)

*Primary Examiner* — Xiao S Zhao
*Assistant Examiner* — Nicholas J Chidiac
(74) *Attorney, Agent, or Firm* — Sughrue Mion, PLLC

(57) ABSTRACT

Disclosed is a method for manufacturing a 3D printing structure, the method including: producing a molded body by performing 3D printing on paste including printing powder in a coagulation bath including a hydrogel; hardening the molded body produced in the coagulation bath; and removing the hydrogel in the coagulation bath. A method for manufacturing a 3D printing structure, which is provided according to an aspect of the disclosure, does not require printing of a separate support, and thus it is possible to save time and costs. A post-processing process for removing a support is not required. Thus, a process is further simplified, and there is no risk of damage to a structure.

18 Claims, 16 Drawing Sheets

(51) Int. Cl.
*B33Y 70/10* (2020.01)
*B33Y 80/00* (2015.01)

(56) References Cited

U.S. PATENT DOCUMENTS

| | | | | |
|---|---|---|---|---|
| 2016/0167312 A1* | 6/2016 | Feinberg | ............... | A61L 27/04 |
| | | | | 264/239 |
| 2017/0361534 A1* | 12/2017 | Fernandez-Nieves | ....................... | |
| | | | | B29C 64/40 |
| 2018/0281295 A1* | 10/2018 | Tibbits | ............... | B29C 64/106 |
| 2019/0375149 A1 | 12/2019 | Limem et al. | | |
| 2020/0047251 A1* | 2/2020 | Song | ............... | B33Y 10/00 |
| 2021/0394391 A1* | 12/2021 | Minary-Jolandan | ... | B33Y 80/00 |
| 2022/0218873 A1* | 7/2022 | Bhowmick | ............ | A61L 27/26 |
| 2022/0241194 A1* | 8/2022 | Tibbitt | ............... | C08G 63/912 |

FOREIGN PATENT DOCUMENTS

| | | | | | |
|---|---|---|---|---|---|
| KR | 10-2018-0055960 A | | 5/2018 | | |
| KR | 20200056282 A | * | 8/2019 | ............ | A61L 27/46 |
| KR | 10-2020-0056282 A | | 5/2020 | | |
| KR | 20200056282 A | | 5/2020 | | |

OTHER PUBLICATIONS

Moxon, Samuel R., et al. "Suspended manufacture of biological structures." Advanced Materials(2017), vol. 29, Article No. 1605594, pp. 1-6.

* cited by examiner

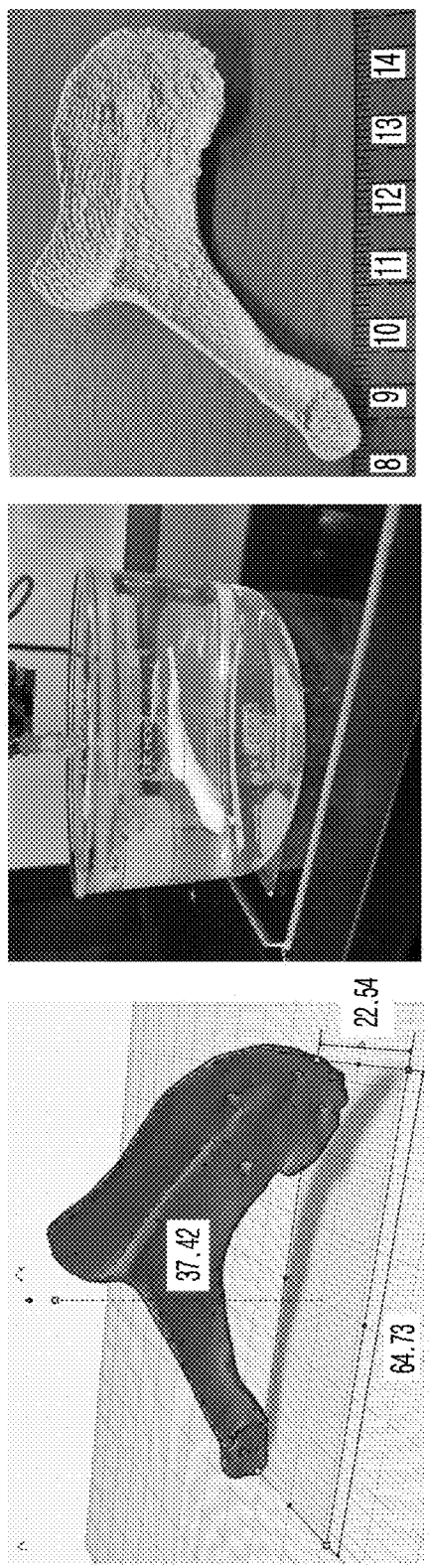

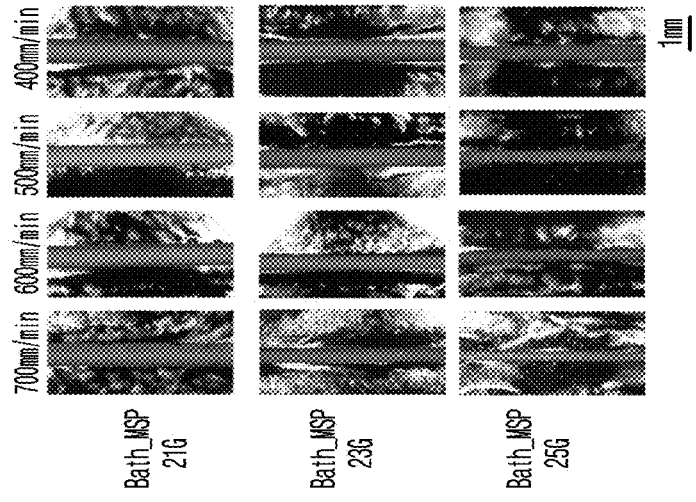
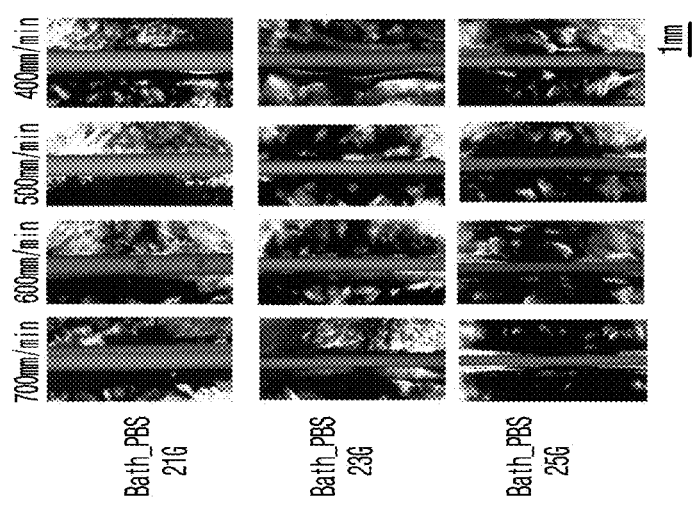
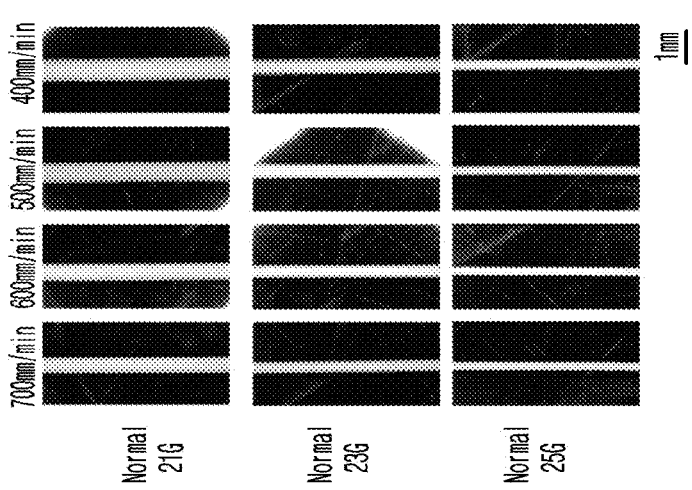

METHOD FOR MANUFACTURING FREESTANDING 3D PRINTING STRUCTURE

CROSS-REFERENCES TO RELATED APPLICATION

This patent application claims the benefit of priority from Korean Patent Application No. 10-2020-0133375 filed on Oct. 15, 2020, the contents of which are incorporated herein by reference.

BACKGROUND OF THE INVENTION

1. Field of the Invention

The disclosure relates to a method for manufacturing a freestanding 3D printing structure.

2. Description of the Related Art

Representative ceramic used as a hard tissue-regenerating material includes calcium phosphate-based ceramic having a chemical similarity to a bone mineral phase. Calcium phosphate-based ceramic is generally present in a powder form. In order to produce a three-dimensional tissue-regenerating support via a 3D printing method by using the calcium phosphate-based ceramic as a raw material, applied is a process of: producing a form by a combination of ceramic powder and an organic binder, removing an organic material via high-temperature sintering (>1000° C.), and forming a bond between ceramic powder particles to obtain a support having structural stability; or producing a three-dimensional form by a polymer, injecting a composite of ceramic powder and an organic binder by using the three-dimensional form as a mold, and then firing the composite at a high temperature to remove the polymer and the organic binder.

Likewise, to produce a three-dimensional support by using ceramic, a high-temperature sintering process is essentially required. However, heating at a high temperature causes unexpected crystallization, degradation of biodegrability and bioactivity due to the unexpected crystallization, and instable mechanical properties due to shrinkage and cracks. Accordingly, a low-temperature process of not heating a ceramic support at a high temperature needs to be developed.

Ceramic powder may be bulked by high-temperature sintering as well as by hydration or acid-base reaction via mixing of powder and a hardening solution. Such a reaction is referred to as a cement reaction. Calcium phosphate is a representative bone cement material and is divided into apatite-based and brucite-based materials according to a result material thereof. However, in the case of calcium phosphate-based cements, specifically, brucite-based cement, it is often pointed out as a limitation that mechanical strength is low and acidity is strong due to phosphoric acid elution during solution immersion. In addition, there is a limitation to the structural control of a three-dimensional molded body due to a rapid hardening reaction.

Likewise, conventionally developed were: a technology of producing calcium phosphate with a controlled three-dimensional form at a low temperature without high-temperature heating (Korean Patent Publication No. 10-2018-0055960); a technology related to a hard tissue-regenerating support including magnesium phosphate (Korean Patent Registration No. 10-1562556); and a method for controlling a hardening speed of a calcium phosphate support (Korean Patent Publication No. 10-2020-0056282). The developed technologies have overcome the technical limitations of applying bone cement to a 3D printing technology by performing 3D printing on paste produced using bone cement raw material powder to produce a three-dimensional form and then inducing a hardening reaction. The technologies have advantages in that sufficient mechanical strength may be secured without performing a high-temperature sintering process and excellent bioactivity and biocompatibility may be ensured.

However, in the case of a complicated 3D structure including an overhang, it is necessary to perform 3D printing together with a support. Thus, a support and a structure are printed together, and this causes limitations (FIG. 1A and FIG. 1B) in that: a longer production time is consumed; a large amount of ceramic materials are consumed to produce the support; and there is a risk of damage to the structure when the support is removed, because a post-processing process for removing the support should be additionally performed.

Bone tissue is composed of not only ceramic, which is an inorganic material, but also organic materials which are extracellular matrixes, blood vessels, and various cells. Accordingly, in order to produce a hard tissue-regenerating support having high regeneration performance, the environment of bone tissue should be simulated as much as possible. A cementation reaction process for ceramic 3D printing provides an unfavorable environment for the survival of cells, and it is difficult to achieve high cell viability. In addition, since an existing 3D printing process prints ink including cells in the air, the survival of cells may be adversely affected if the 3D printing process continues for a long time.

Accordingly, a study for 3D printing of a complicated structure which can achieve high cell viability and does not require printing of a separate support has become necessary.

SUMMARY OF THE INVENTION

The disclosure is to provide: a method for manufacturing a 3D printing structure, whereby a complicated structure may be produced even without printing a support; and a method for manufacturing a ceramic/cell 3D printing structure having high cell viability.

In an aspect of the disclosure, disclosed is a method for manufacturing a 3D printing structure, the method including: producing a molded body by performing 3D printing on paste including printing powder in a coagulation bath including a hydrogel; hardening the molded body produced in the coagulation bath; and removing the hydrogel in the coagulation bath.

In an example, the coagulation bath may further include a hardening agent.

In another example, the paste may further include a photocurable resin, and the hardening of the molded body produced in the coagulation bath may be performed by radiating light.

A method for manufacturing a 3D printing structure, which is provided according to an aspect of the disclosure, does not require printing of a separate support, and thus it is possible to save time and costs. A post-processing process for removing a support is not required. Thus, a process is further simplified, and there is no risk of damage to a structure.

BRIEF DESCRIPTION OF THE DRAWINGS

The above and other objects, features and other advantages of the present invention will be more clearly understood from the following detailed description taken in conjunction with the accompanying drawings, in which:

FIG. 9A shows dimensions of a ceramic 3D printing structure and FIG. 9B and FIG. 9C show ceramic 3D printing structures manufactured according to an another example;

FIG. 12A, FIG. 12B, and FIG. 12C show images of nozzle size-specific resolutions depending on a printing speed, according to an experimental example;

DESCRIPTION OF THE PREFERRED EMBODIMENTS

Figure 1:
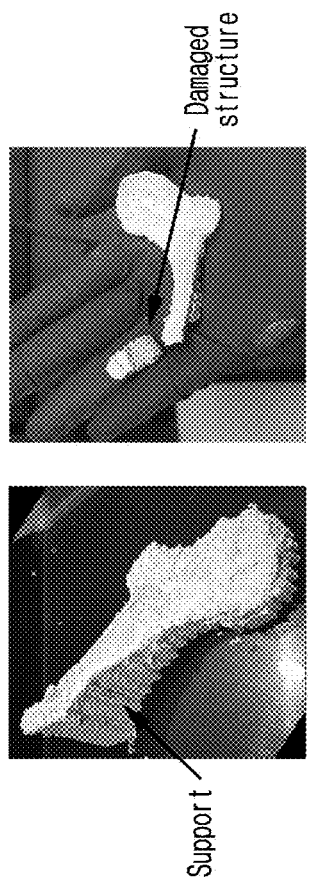
FIG. 1A and FIG. 1B show images of a ceramic 3D printing structure on which a support is printed together via an existing method.
Figure 2:
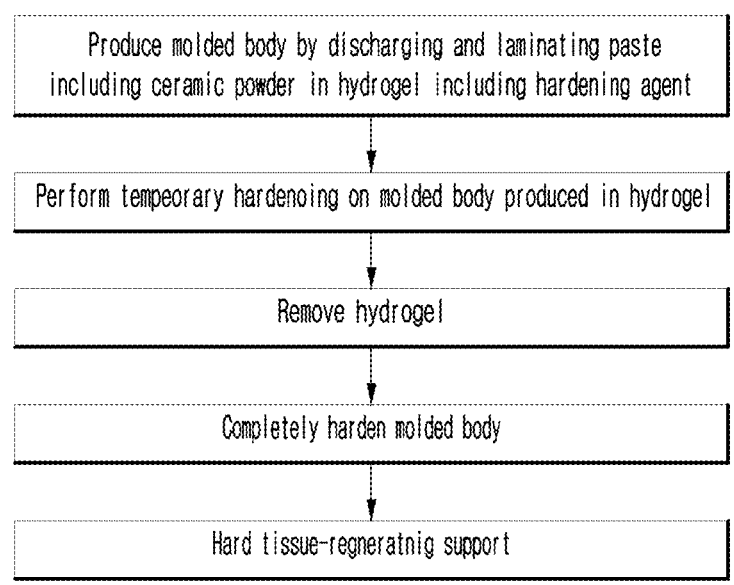
FIG. 2 is a flowchart typically showing a method for manufacturing a 3D printing structure, according to an example.

Various changes may be made in the disclosure, and various examples may be made accordingly. Thus, specific examples will be presented below and described in detail.

In addition, all terms which are not specifically defined in the present specification may be used in a meaning that can be understood by all those skilled in the art to which the disclosure belongs.

However, it is to be construed that the disclosure is not intended to be limited only to specific examples to be described below, but includes all modifications, equivalents, and substitutes included in the spirit and technical scope of the disclosure.

Therefore, there may be other equivalents and modifications different from examples described herein, and examples presented herein are merely the most preferable examples.

In an aspect of the disclosure, provided is a method for manufacturing a 3D printing structure, the method including: producing a molded body by performing 3D printing on paste including printing powder in a coagulation bath including a hydrogel; hardening the molded body produced in the coagulation bath; and removing the hydrogel in the coagulation bath.

In an example in accordance therewith, provided is a method for manufacturing a 3D printing structure, the method including: producing a molded body by performing 3D printing on paste including printing powder in a coagulation bath including a hardening agent and a hydrogel; hardening the molded body produced in the coagulation bath; and removing the hydrogel in the coagulation bath.

Hereinafter, a manufacturing method of an example of a method for manufacturing a 3D printing structure, which is provided in an aspect of the disclosure, will be described in detail with reference to steps.

A method for manufacturing a 3D printing structure, which is provided in an example, includes a step of producing a molded body by performing 3D printing on paste including printing powder in a coagulation bath.

The coagulation bath includes a hardening agent and a hydrogel.

The hydrogel may include one or more materials selected from the group consisting of Pluronic F-127 (PF-127), gelatin, poly(N-isopropylacrylamide), agarose, carrageenan, gellan gum, xanthan gum, alginate, Carbopol, and Laponite nanoclay.

The hydrogel may include, in a concentration of 0.1 to 40 wt %, the one or more materials selected from the group consisting of Pluronic F-127 (PF-127), gelatin, poly(N-isopropylacrylamide), agarose, carrageenan, gellan gum, xanthan gum, alginate, Carbopol, and Laponite nanoclay. If the one or more materials are included in a concentration of less than 0.1 wt %, this may cause a problem in which mechanical properties for supporting printed paste are low and thus a structure collapses. If the one or more materials are included in a concentration of more than 40 wt %, this may cause a problem in which paste is not printed smoothly because the rigidity of the hydrogel increases and the movement of a 3D printing nozzle is disturbed.

The hydrogel may further include an additive.

The additive may be one or more selected from the group consisting of a cell culture medium, thrombin, calcium chloride, and calcium carbonate.

The printing powder may be metal powder or ceramic powder.

The ceramic powder may be magnesium phosphate-based ceramic powder including one or more magnesium sources selected from the group consisting of MgO, $Mg_3(PO_4)_2$, $Mg(OH)_2$, $MgCl_2$, and $MgSO_4$ and one or more phosphoric acid sources selected from the group consisting of $NH_4H_2PO_4$, $(NH_4)_2HPO_4$, $KH_2PO_4$, $K_2HPO_4$, and $NaH_2PO_4$.

At this time, the hardening agent may be one or more selected from the group consisting of diammonium hydrogen phosphate (DAHP), $NH_4H_2PO_4$, $KH_2PO_4$, $K_2HPO_4$, and $NaH_2PO_4$.

In addition, the ceramic powder may be calcium phosphate-based ceramic powder which is one or more selected from the group consisting of α-tricalcium phosphate (α-TCP), β-tricalcium phosphate, hydroxyapatite, dicalcium phosphate dehydrate (DCPD), monocalcium phosphate monohydrate (MCPM), dicalcium phosphate anhydrous (DCPA), and biphasic calcium phosphate (BCP).

At this time, the hardening agent may be one or more selected from the group consisting of disodium phosphate dihydrate (DSP, $Na_2HPO_4 \cdot 2H_2O$), monosodium phosphate dehydrate (MSP, $NaH_2PO_4 \cdot 2H_2O$), phosphate buffer saline (PBS), and monocalcium phosphates monohydrate (MCPM, $Ca(H_2PO_4)_2 \cdot H_2O$).

The paste may further include a thickening agent.

The thickening agent may be one or more selected from the group consisting of hydroxypropyl methylcellulose (HPMC), hydroxyethyl cellulose (HEC), methyl cellulose, carboxymethyl cellulose (CMC), alginate, gelatin, silk fibroin, collagen, fibrinogen, chitosan, agar, Matrigel, a decellularized extracellular matrix, starch, pectin, polyvinyl alcohol, polyurethane, poly(ethylene glycol), poly(propylene glycol), hyaluronan, and poly(vinylpyrrolidone).

The paste may further include one or more alcohols selected from the group consisting of methanol, ethanol, propanol, and butanol.

The paste may further include cells.

Here, if the paste further includes cells, the paste may further include a cell culture medium.

The cells may be one or more selected from the group consisting of human bone marrow-derived mesenchymal stem cells, adipose-derived mesenchymal stem cells, induced pluripotent stem cells, vascular endothelial cells, osteoblasts, chondrocytes, fibroblasts, and a mixture thereof.

The paste may further include a biofunctional material.

The biofunctional material may be one or more selected from the group consisting of a growth factor, a protein, a protein drug, an antiproliferative agent, antithrombin, an immunosuppressant, a lipid, an antilipid, a liposome, an anti-inflammatory agent, an antitumor agent, an antiplatelet agent, an angiogenic agent, an antiangiogenic agent, a vitamin, an aptamer, an antimitotic agent, a metalloproteinase inhibitor, an NO donor, estradiol, an antisclerosing agent, a vasoactive agent, a beta blocking agent, an AZ blocking agent, a hormone, statins, an antioxidant agent, a membrane stabilizer, a calcium antagonist, retinoid, a peptide, a lipoprotein, a polypeptide, a polynucleotide encoding polypeptide, an enzyme, a genetic material, a chemical solvent, an energy-activator, a lymphocyte inhibiting material, a macrophage inhibiting material, and a mixture thereof.

In the step described above, the paste may be obtained as a molded body of a three-dimensional structure via a 3D printing technology. The 3D printing technology is a technology in which a digitized three-dimensional product design is continuously reconstructed into two-dimensional sections and then raw materials are printed layer by layer so as to manufacture a product.

The thickness of a column of a support may be adjusted by using nozzles of various sizes applied to a 3D printer, and various forms (column spacing, pore sizes, pore forms, support forms, and the like) may be molded via a computer program.

Next, a method for manufacturing a 3D printing structure, which is provided in an example, includes a step of hardening a molded body produced in a coagulation bath.

The hardening may begin simultaneously with the printing of paste.

At this time, hardening performed simultaneously with the printing of paste may be referred to as temporary hardening.

Via the temporary hardening, the physical properties of a molded body may be secured.

The temporary hardening may be performed at a temperature of 20° C. to 70° C. If the temporary hardening is performed at a temperature of less than 20° C., this may cause a problem in which a 3D printing structure has lower mechanical properties due to an insufficient cement reaction of paste and thus the structure may collapses when a coagulation bath is removed.

If paste further includes cells or a biofunctional material, it is preferable to perform the temporary hardening at a temperature of less than 20° C. This is because if the temporary hardening is performed at a temperature of more than 37° C., this may cause a problem in which cell death occurs or bioactivities are degraded.

In the step described above, it is preferable that a hydrogel in the coagulation bath is maintained in the form of gel. The coagulation bath includes a hydrogel having comparatively high viscosity. Thus, even if a separate support is not printed, the hydrogel, in place of a support, may support a molded body.

In an example, the viscosity of the hydrogel may be $10^4$ Pa or more, and preferably $10^4$ Pa or more.

In addition, the temporary hardening may be performed for 30 minutes or more. If the temporary hardening is performed for less than 30 minutes, this may cause a problem in which a cement reaction of paste is not sufficient.

If paste further includes cells or a biofunctional material, it is preferable to perform the temporary hardening for 30 minutes to 1 hour. This is because if the temporary hardening is performed for more than 1 hour, this may cause a problem in which cell death occurs or bioactivities are degraded.

Next, a method for manufacturing a 3D printing structure, which is provided in an example, includes a step of removing a hydrogel in a coagulation bath.

The step of removing a hydrogel in a coagulation bath may include one or more among: solating the hydrogel and then removing the coagulation bath; dissociating the crosslinking of the hydrogel which has been crosslinked; and introducing the coagulation bath into a buffer and dissolving the coagulation bath.

Otherwise, if a soft hydrogel is used, the hydrogel may be removed and a molded body may be separated without separate processing.

If the step of removing a hydrogel in a coagulation bath is performed by the solating of the hydrogel and the removing of the coagulation bath, the solating may be performed by one or more among schemes including temperature adjustment and pH adjustment.

For example, pluronic F-127 (PF-127), gelatin, agarose, and poly(N-isopropylacrylamide) are materials having temperature sensitivity, and solation may be induced by adjusting the temperature thereof.

In an example, in the case of PF-127, a phase change into sol occurs at a temperature of about 20° C. or less, and a gel state is maintained at a temperature of about 20° C. or more. Therefore, by reducing the temperature to about 20° C. or less, solation of a hydrogel may be induced. At this time, it is preferable that PF-127 is included in a concentration of 10 to 30 wt % in a hydrogel.

In another example, gelatin is in a gel state at a temperature of about 20° C. or less and is present in a sol state at a temperature of about 20° C. or more. Therefore, by increasing the temperature to about 20° C. or more, solation of a hydrogel may be induced. At this time, it is preferable that gelatin is included in a concentration of 5 to 20 wt % in a hydrogel.

Likewise, a temperature is properly changed by using materials having temperature sensitivity, and thus solation of a hydrogel may be induced.

In addition, for example, Carbopol is a material using pH sensitivity, and solation may be induced by adjusting the pH thereof.

Carbopol is in a sol state in an acid environment and is in a gel state at pH 7.4. Thus, by adjusting the pH to 7.4 or less, solation of a hydrogel may be induced.

At this time, it is preferable that Carbopol is included in a concentration of 0.5 to 2 wt % in a hydrogel.

As described above, if a hydrogel is solated, the viscosity of a coagulation bath may be 10 Pa or less, preferably 5 Pa or less, and more preferably 1 Pa or less.

The step of removing a hydrogel in a coagulation bath may also be performed by the dissociating of the crosslinking of a hydrogel which has been crosslinked.

For example, carrageenan, gellan gum, xanthan gum, and alginate are materials using ion crosslinking. By crosslinking all these materials by $CaCl_2$, performing printing on crosslinked gel, and then dissociating the crosslinking by Tris-HCL, a hydrogel may be removed.

At this time, it is preferable that: carrageenan is included in a concentration of 1 to 5 wt % in a hydrogel; gellan gum is included in a concentration of 0.5 to 1 wt % in a hydrogel; xanthan gum is included in a concentration of 0.1 to 0.5 wt % in a hydrogel; and alginate is included in a concentration of 0.5 to 2 wt % in a hydrogel.

In addition, the step of removing a hydrogel in a coagulation bath may also be performed by the introducing of the coagulation bath into a buffer and the dissolving of the coagulation bath.

For example, if a hydrogel including Carbopol, agarose, or Laponite nanoclay is used, a hydrogel may be removed by introducing a coagulation bath into a buffer such as PBS and dissolving the coagulation bath.

In addition, if a hydrogel including alginate is used, the hydrogel may be removed via a scheme of melting the hydrogel by using alginate lyase.

Furthermore, in the step of removing a hydrogel in a coagulation bath, the hydrogel may be removed and a molded body may be separated without separate processing.

For example, agarose and Laponite nanoclay are soft gel materials. If a hydrogel including these materials is used, a molded body may be separated by removing the hydrogel after the production and temporary hardening of the molded body. At this time, it is preferable that agarose is included in a concentration of 0.1 to 1 wt % in a hydrogel and laponite is included in a concentration of 1 to 5 wt %.

Likewise, a 3D printing structure may be obtained by removing a coagulation bath via various schemes.

In the step described above, washing of a 3D printing structure may be further included. The washing may be performed by using distilled water or phosphate buffer saline.

In addition, a method for manufacturing a 3D printing structure, which is provided in an example, may further include a step of completely hardening a molded body after removing a hydrogel in a coagulation bath.

A hardening liquid used for the complete hardening may be one or more selected from the group consisting of disodium phosphate dehydrate (DSP, $Na_2HPO_4 \cdot 2H_2O$), monosodium phosphate dihydrate (MSP, $NaH_2PO_4 \cdot 2H_2O$), phosphate buffer saline (PBS), monocalcium phosphates monohydrate (MCPM, $Ca(H_2PO_4)_2 \cdot H_2O$), and a cell culture medium.

The hardening may be performed at a temperature of 20° C. to 60° C. If the hardening is performed at a temperature of less than 20° C., this may cause a problem in which a 3D printing structure has lower mechanical properties due to an insufficient cement reaction of paste and thus the structure may collapses when a coagulation bath is removed. If paste further includes cells or a biofunctional material, it is preferable to perform the hardening at 37° C. by using a cell culture medium as a hardening liquid.

A 3D printing structure produced by a method for manufacturing a 3D printing structure, which is provided in an example, may at least partially include an overhang structure.

An overhang structure refers to a structure in which 3D printing becomes unstable as the amount of overlap between lower and upper layers decreases. For example, the inclination of an overhang portion may be 30° or more and, more specifically, 45° or more.

If a 3D printing structure having an overhang structure is manufactured via an existing process, a scheme of performing printing together with a support and then removing the support later is adopted. However, a method for manufacturing a 3D printing structure, which is provided in an example, does not require the printing of a support.

Accordingly, it is possible to save time and costs. A post-processing process for removing a support is not required. Thus, a process is further simplified, and there is no risk of damage to a structure.

The 3D printing structure may be a ceramic printing structure or a metal printing structure.

The 3D printing structure may be, for example, a hard tissue-regenerating support.

In addition, the 3D printing structure may be a composite structure including ceramic and a biofunctional material together.

Here, the composite structure suffices to include both ceramic and a biofunctional material, and is not limited to a specific form.

For example, the composite structure may be in a form in which a biofunctional material is located in a ceramic structure, a form in which one among a biofunctional material and ceramic is coated on the surface of the other, or a form of a core-shell structure.

As described above, the composite structure may be produced by using paste including both ceramic powder and a biofunctional material, and may be produced by respectively printing ceramic powder and a biofunctional material from separate nozzles.

In addition, in another example, provided is a method for manufacturing a 3D printing structure, the method including: producing a molded body by performing 3D printing on paste including printing powder and a photocurable resin in a coagulation bath including a hydrogel; hardening, by radiating light, the molded body produced in the coagulation bath; and removing the hydrogel in the coagulation bath.

A method for manufacturing a 3D printing structure, which is provided in another example, includes a step of producing a molded body by performing 3D printing on paste including printing powder in a coagulation bath.

The coagulation bath includes a hydrogel.

The hydrogel may include one or more materials selected from the group consisting of Pluronic F-127 (PF-127), Pluronic P-123 (P-123), gelatin, poly(N-isopropylacrylamide), agarose, carrageenan, gellan gum, xanthan gum, alginate, Carbopol, and Laponite nanoclay.

The hydrogel may include, in a concentration of 0.1 to 40 wt %, the one or more materials selected from the group consisting of Pluronic F-127 (PF-127), Pluronic P-123 (P-123), gelatin, poly(N-isopropylacrylamide), agarose, carrageenan, gellan gum, xanthan gum, alginate, Carbopol, and Laponite nanoclay. If the one or more materials are included in a concentration of less than 0.1 wt %, this may cause a problem in which mechanical properties for supporting printed paste are low and thus a structure collapses. If the one or more materials are included in a concentration of more than 40 wt %, this may cause a problem in which paste is not printed smoothly because the rigidity of the hydrogel increases and the movement of a 3D printing nozzle is disturbed.

The hydrogel may further include an additive.

The additive may be one or more selected from the group consisting of a cell culture medium, thrombin, calcium chloride, and calcium carbonate.

The printing powder may be ceramic powder or metal powder.

The ceramic powder may be magnesium phosphate-based ceramic powder including one or more magnesium sources selected from the group consisting of MgO, $Mg_3(PO_4)_2$, $Mg(OH)_2$, $MgCl_2$, and $MgSO_4$ and one or more phosphoric acid sources selected from the group consisting of $NH_4H_2PO_4$, $(NH_4)_2HPO_4$, $KH_2PO_4$, $K_2HPO_4$, and $NaH_2PO_4$.

In addition, the ceramic powder may be calcium phosphate-based ceramic powder which is one or more selected from the group consisting of α-tricalcium phosphate (α-TCP), β-tricalcium phosphate, hydroxyapatite, dicalcium phosphate dehydrate (DCPD), monocalcium phosphate monohydrate (MCPM), dicalcium phosphate anhydrous (DCPA), and biphasic calcium phosphate (BCP).

Furthermore, the ceramic powder may be powder which is one or more selected from the group consisting of alumina, zirconia, titania, silica, yttria, bioglass, silicon nitride, carbon nitride, and aluminum carbide.

In addition, the metal powder may be powder which is one or more selected from the group consisting of stainless steel and $Ti_6Al_4V$.

The paste may further include a photocurable polymer.

The photocurable polymer may include one or more selected from the group consisting of PEGDA, HDDA, Laromer, TEGDMA, PPGDA, TMPTA, alginate-methacrylate, gelatin-methacrylate, hyaluronic acid methacrylate, and collagen-methacrylate.

At this time, if alginate-metharylate is used as the photocurable polymer, the coagulation bath may further include $CaCl_2$.

The paste may further include a thickening agent.

The thickening agent may be one or more selected from the group consisting of hydroxypropyl methylcellulose (HPMC), hydroxyethyl cellulose (HEC), methyl cellulose, carboxymethyl cellulose (CMC), Pluronic F-127 (PF-127), Pluronic P-123 (P-123), alginate, gelatin, silk fibroin, collagen, fibrinogen, chitosan, agar, Matrigel, a decellularized extracellular matrix, starch, pectin, polyvinyl alcohol, polyurethane, poly(ethylene glycol), poly(propylene glycol), hyaluronan, and poly(vinylpyrrolidone).

The paste may further include one or more alcohols selected from the group consisting of methanol, ethanol, propanol, and butanol.

The paste may further include cells.

Here, if the paste further includes cells, the paste may further include a cell culture medium.

The cells may be one or more selected from the group consisting of human bone marrow-derived mesenchymal stem cells, adipose-derived mesenchymal stem cells, induced pluripotent stem cells, vascular endothelial cells, osteoblasts, chondrocytes, fibroblasts, and a mixture thereof.

The paste may further include a biofunctional material.

The biofunctional material may be one or more selected from the group consisting of a growth factor, a protein, a protein drug, an antiproliferative agent, antithrombin, an immunosuppressant, a lipid, an antilipid, a liposome, an anti-inflammatory agent, an antitumor agent, an antiplatelet agent, an angiogenic agent, an antiangiogenic agent, a vitamin, an aptamer, an antimitotic agent, a metalloproteinase inhibitor, an NO donor, estradiol, an antisclerosing agent, a vasoactive agent, a beta blocking agent, an AZ blocking agent, a hormone, statins, an antioxidant agent, a membrane stabilizer, a calcium antagonist, retinoid, a peptide, a lipoprotein, a polypeptide, a polynucleotide encoding polypeptide, an enzyme, a genetic material, a chemical solvent, an energy-activator, a lymphocyte inhibiting material, a macrophage inhibiting material, and a mixture thereof.

If the paste further include cells or a biofunctional material, it is preferable that the photocurable polymer is one or more selected from the group consisting of PEGDA, alginate-methacrylate, gelatin-methacrylate, hyaluronic acid methacrylate, and collagen-methacrylate.

In the step described above, the paste may be obtained as a molded body of a three-dimensional structure via a 3D printing technology. The 3D printing technology is a technology in which a digitized three-dimensional product design is continuously reconstructed into two-dimensional sections and then raw materials are printed layer by layer so as to manufacture a product.

The thickness of a column of a support may be adjusted by using nozzles of various sizes applied to a 3D printer, and various forms (column spacing, pore sizes, pore forms, support forms, and the like) may be molded via a computer program.

Next, a method for manufacturing a 3D printing structure, which is provided in another example, includes a step of hardening a molded body produced in a coagulation bath.

The hardening may be photocuring performed by radiating light.

The light may be UV.

Via the hardening, the physical properties of a molded body may be secured.

In the step described above, it is preferable that a hydrogel in the coagulation bath is maintained in the form of gel. The coagulation bath includes a hydrogel having comparatively high viscosity. Thus, even if a separate support is not printed, the hydrogel, in place of a support, may support a molded body.

In an example, the viscosity of the hydrogel may be $10^4$ Pa or more, and preferably $10^4$ Pa or more.

In addition, the photocuring may be performed for 1 second or more. If the photocuring is performed for less than 1 second, this may cause a problem in which a photocuring reaction of paste is not sufficient.

If paste further includes cells or a biofunctional material, it is preferable to perform the photocuring for 1 second to 2 minutes. This is because if the photocuring is performed for more than 2 minutes, this may cause a problem in which cell death occurs or bioactivities are degraded.

Next, a method for manufacturing a 3D printing structure, which is provided in an example, includes a step of removing a hydrogel in a coagulation bath.

The step of removing a hydrogel in a coagulation bath may include one or more among: solating the hydrogel and then removing the coagulation bath; dissociating the crosslinking of the hydrogel which has been crosslinked; and introducing the coagulation bath into a buffer and dissolving the coagulation bath.

Otherwise, if a soft hydrogel is used, the hydrogel may be removed and a molded body may be separated without separate processing.

If the step of removing a hydrogel in a coagulation bath is performed by the solating of the hydrogel and the removing of the coagulation bath, the solating may be performed by one or more among schemes including temperature adjustment and pH adjustment.

For example, pluronic F-127 (PF-127), gelatin, agarose, and poly(N-isopropylacrylamide) are materials having temperature sensitivity, and solation may be induced by adjusting the temperature thereof.

In an example, in the case of PF-127, a phase change into sol occurs at a temperature of about 20° C. or less, and a gel state is maintained at a temperature of about 20° C. or more. Therefore, by reducing the temperature to about 20° C. or less, solation of a hydrogel may be induced. At this time, it is preferable that PF-127 is included in a concentration of 10 to 30 wt % in a hydrogel.

In another example, PF-123 is in a sol state at a temperature of about 4° C. or less and is present in a gel state at a temperature of about 4° C. or more. In addition, P-123 is present in a sol state at 37° C. Therefore, by adjusting the temperature to about 4° C. or less or to 37° C. or more, solation of a hydrogel may be induced. At this time, it is preferable that P-123 is included in a concentration of 10 to 30 wt % in a hydrogel.

In still another example, gelatin is in a gel state at a temperature of about 20° C. or less and is present in a sol state at a temperature of about 20° C. or more. Therefore, by increasing the temperature to about 20° C. or more, solation of a hydrogel may be induced. At this time, it is preferable that gelatin is included in a concentration of 5 to 20 wt % in a hydrogel.

Likewise, a temperature is properly changed by using materials having temperature sensitivity, and thus solation of a hydrogel may be induced.

In addition, for example, Carbopol is a material using pH sensitivity, and solation may be induced by adjusting the pH thereof.

Carbopol is in a sol state in an acid environment and is in a gel state at pH 7.4. Thus, by adjusting the pH to 7.4 or less, solation of a hydrogel may be induced.

At this time, it is preferable that Carbopol is included in a concentration of 0.5 to 2 wt % in a hydrogel.

As described above, if a hydrogel is solated, the viscosity of a coagulation bath may be 10 Pa or less, preferably 5 Pa or less, and more preferably 1 Pa or less.

The step of removing a hydrogel in a coagulation bath may also be performed by the dissociating of the crosslinking of a hydrogel which has been crosslinked.

For example, carrageenan, gellan gum, xanthan gum, and alginate are materials using ion crosslinking. By crosslinking all these materials by $CaCl_2$, performing printing on crosslinked gel, and then dissociating the crosslinking by Tris-HCL, a hydrogel may be removed.

At this time, it is preferable that: carrageenan is included in a concentration of 1 to 5 wt % in a hydrogel; gellan gum is included in a concentration of 0.5 to 1 wt % in a hydrogel; xanthan gum is included in a concentration of 0.1 to 0.5 wt % in a hydrogel; and alginate is included in a concentration of 0.5 to 2 wt % in a hydrogel.

In addition, the step of removing a hydrogel in a coagulation bath may also be performed by the introducing of the coagulation bath into a buffer and the dissolving of the coagulation bath.

For example, if a hydrogel including Carbopol, agarose, or Laponite nanoclay is used, a hydrogel may be removed by introducing a coagulation bath into a buffer such as PBS and dissolving the coagulation bath.

In addition, if a hydrogel including alginate is used, the hydrogel may be removed via a scheme of melting the hydrogel by using alginate lyase.

Furthermore, in the step of removing a hydrogel in a coagulation bath, the hydrogel may be removed and a molded body may be separated without separate processing.

For example, agarose and Laponite nanoclay are soft gel materials. If a hydrogel including these materials is used, a molded body may be separated by removing the hydrogel after the production and temporary hardening of the molded body. At this time, it is preferable that agarose is included in a concentration of 0.1 to 1 wt % in a hydrogel and laponite is included in a concentration of 1 to 5 wt %.

Likewise, a 3D printing structure may be obtained by removing a coagulation bath via various schemes.

In the step described above, washing of a 3D printing structure may be further included. The washing may be performed by using distilled water or phosphate buffer saline.

In addition, in a method for manufacturing a 3D printing structure, which is provided in another example, if the 3D printing structure includes a plurality of layers, the performing of the 3D printing on the paste including printing powder and the hardening of the molded body by radiating light may be repeated multiple times.

Likewise, a process of performing hardening layer by layer and then performing lamination is performed, and thus printing may be achieved in various structures.

In addition, a method for manufacturing a 3D printing structure, which is provided in another example, may further include a step of heating a molded body after removing a hydrogel in a coagulation bath.

In the step described above, the heating may be performed to sinter a ceramic or metal molded body.

A method for manufacturing a 3D printing structure, which is provided in another example, is advantageous in that relatively various materials are applicable compared to a scheme of using self-hardening.

A 3D printing structure produced by a method for manufacturing a 3D printing structure, which is provided in an example, may at least partially include an overhang structure.

An overhang structure refers to a structure in which 3D printing becomes unstable as the amount of overlap between lower and upper layers decreases. For example, the inclination of an overhang portion may be 30° or more and, more specifically, 45° or more.

If a 3D printing structure having an overhang structure is manufactured via an existing process, a scheme of performing printing together with a support and then removing the support later is adopted. However, a method for manufacturing a 3D printing structure, which is provided in an example, does not require the printing of a support.

Accordingly, it is possible to save time and costs. A post-processing process for removing a support is not required. Thus, a process is further simplified, and there is no risk of damage to a structure.

The 3D printing structure may be a ceramic 3D printing structure or a metal 3D printing structure.

The ceramic 3D printing structure may be, for example, a hard tissue-regenerating support.

In addition, the ceramic 3D printing structure may be a composite structure including ceramic and a biofunctional material together.

Here, the composite structure suffices to include both ceramic and a biofunctional material, and is not limited to a specific form.

For example, the composite structure may be in a form in which a biofunctional material is located in a ceramic structure, a form in which one among a biofunctional material and ceramic is coated on the surface of the other, or a form of a core-shell structure.

As described above, the composite structure may be produced by using paste including both ceramic powder and a biofunctional material, and may be produced by respectively printing ceramic powder and a biofunctional material from separate nozzles.

Hereinafter, the disclosure will be described in detail with reference to examples and experimental examples.

Examples and experimental examples below are merely to explain the disclosure, and the content of the disclosure is not limited by the examples and experimental examples below.

PRODUCTION EXAMPLE 1

Preparation of Hydrogen 1

Mono sodium phosphate (MSP) was used as a hardening liquid for inducing cementation of ink, and 10 to 30 wt % of Pluronic™ F-127 (PF-127) was added to 1 to 5 wt % of MSP.

PRODUCTION EXAMPLE 2

Preparation of Hydrogel 2

Phosphate buffer saline (PBS) was used as a hardening liquid for inducing cementation of ink, and 10 to 30 wt % of Pluronic™ F-127 (PF-127) was added to 1× PBS.

EXAMPLE 1

3D Printing Structure Printing 1

Paste including α-TCP as ceramic powder and hydroxypropyl methyl cellulose (HPMC) as a thickener was prepared. The ratio of the ceramic powder (powder) to the thickener (liquid) was set to be 10:6 to 10:3.

The paste was put into an extrusion container, and a three-dimensional support was molded in a hydrogel tank of production example 1 by using a 3D printer. Temporary hardening was performed at 37° C. for 30 minutes on the support molded in the hydrogel tank.

Thereafter, the temperature of the hydrogel was adjusted to about 20° C. or less, and the hydrogel was exposed for 20 minutes, so that the hydrogel was solated. The hydrogel accordingly converted into an aqueous solution state was removed, and a molded body was washed.

Then, the molded body was completely hardened at 37° C. for 72 hours by using PBS as a hardening liquid, and thus a three-dimensional support was obtained.

EXAMPLE 2

3D Printing Structure Printing 2

A three-dimensional support was produced in the same manner as in example 1, except that the three-dimensional support was molded in a hydrogel tank of production example 2, not production example 1.

<COMPARATIVE EXAMPLE 1

The same paste as in example 1 was used. The paste was put into an extrusion container, and a three-dimensional support was first produced by using a 3D printer. Then, the support was dried at a temperature of 37° C. for 24 hours.

Thereafter, a hardening reaction was induced by immersing the support produced in the previous step in a corresponding solution for 0 to 48 hours by using a disodium phosphate dihydrate (MSP) aqueous solution as a hardening liquid.

Then, the support was washed, and thus a final three-dimensional support was obtained.

COMPARATIVE EXAMPLE 2

A three-dimensional support was produced in the same manner as in comparative example 1, except that a 1× phosphate buffer saline (PBS) aqueous solution was used as a hardening liquid.

EXAMPLE 1

Analysis on the Viscosity Properties of a Solution Including a Hardening Agent

The viscosity properties of the hardening liquids in production example 1 and production example 2 were analyzed.

Figure 3:
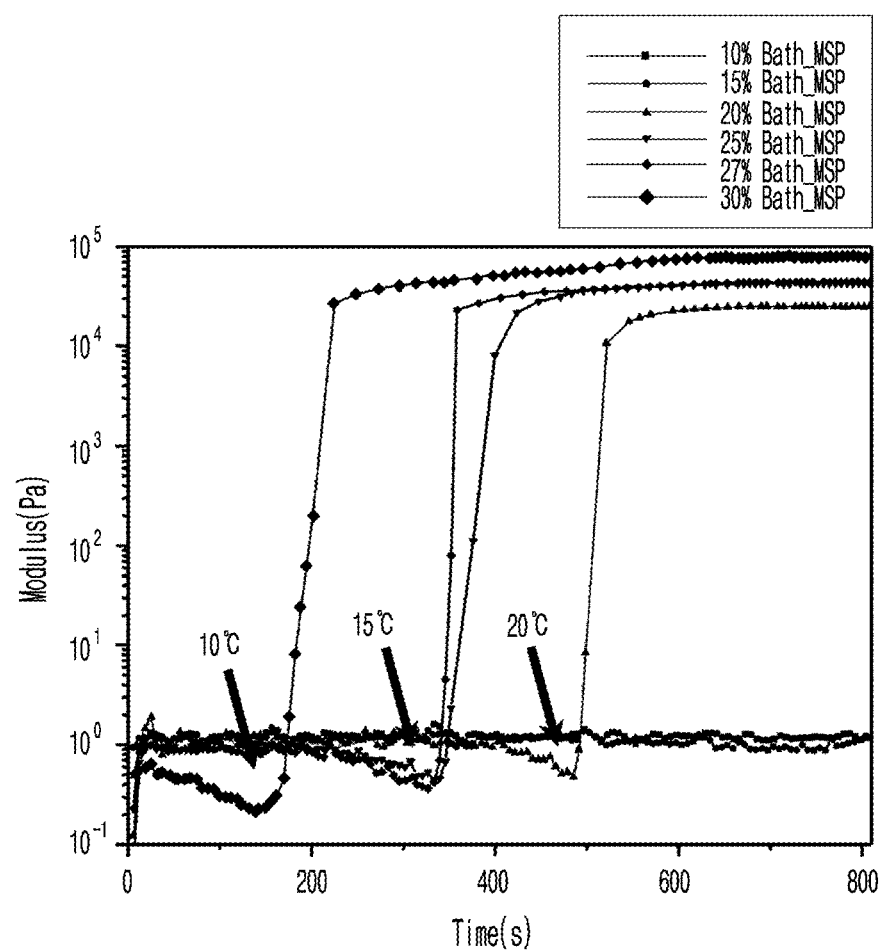
FIG. 3 is a graph showing the concentration-specific viscosity properties of a production example, according to an experimental example.

FIG. 3 shows changes in viscosity when a temperature is changed into 4 to 37° C. while a concentration varies with respect to production example 1.

In FIG. 3, it is possible to confirm that viscosity does not change significantly in the case of MSP having a concentration of 10 wt % or 15 wt % but viscosity changes significantly at a specific temperature in a concentration of 20 wt % or more. This means that a phase transition does not occur in a concentration of 10 wt % or 15 wt % but in a concentration of 20 wt % or more, a phase transition occurs from low-viscosity sol to high-viscosity gel at a specific temperature.

It is possible to confirm that a phase transition occurs at approximately 20° C. in a concentration of 20 wt %, at approximately 15° C. in a concentration of 25 wt % or 27 wt %, and at approximately 10° C. in a concentration of 30 wt %.

Figure 4:
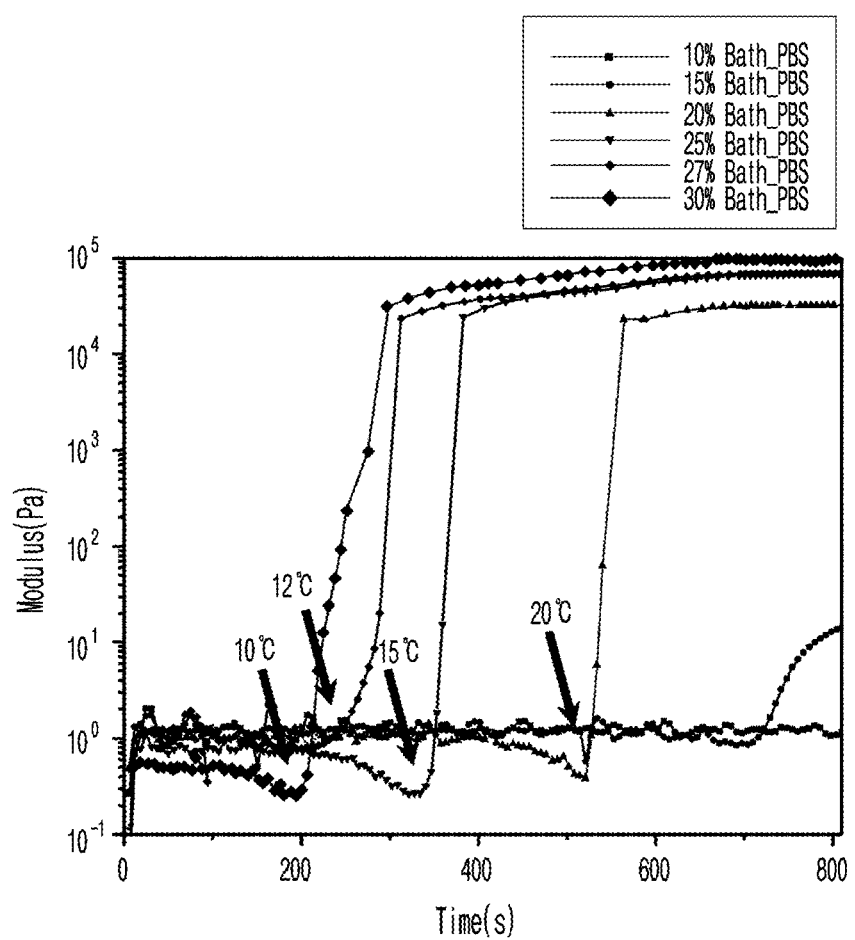
FIG. 4 is a graph showing the concentration-specific viscosity properties of a production example, according to an experimental example.

FIG. 4 shows changes in viscosity when a temperature is changed into 4° C. to 37° C. while a concentration varies with respect to production example 2.

In FIG. 4, it is possible to confirm that viscosity does not change significantly in the case of PBS having a concentration of 10 wt % or 15 wt % but viscosity changes significantly at a specific temperature in a concentration of 20 wt % or more. This means that a phase transition does not occur in a concentration of 10 wt % or 15 wt % but in a concentration of 20 wt % or more, a phase transition occurs from low-viscosity sol to high-viscosity gel at a specific temperature.

It is possible to confirm that a phase transition occurs at approximately 20° C. in a concentration of 20 wt %, at approximately 15° C. in a concentration of 25 wt %, at approximately 12° C. in a concentration of 27 wt %, and at approximately 10° C. in a concentration of 30 wt %.

EXAMPLE 2

Analysis on the Properties of a Produced Three-Dimensional Support

Figure 5:
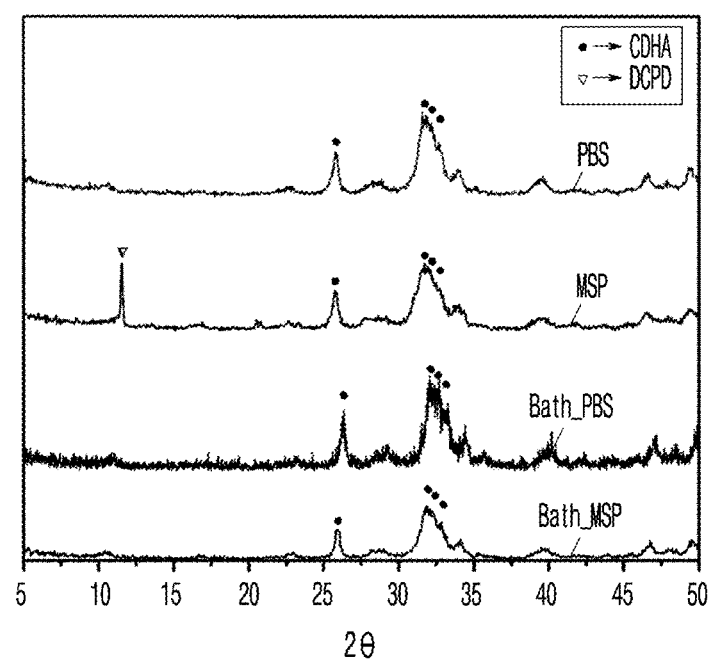
FIG. 5 shows XRD result values of crystal phase changes of structures obtained in examples, according to an experimental example.

Crystal phase changes of the three-dimensional supports produced in example 1 and example 2 were confirmed via X-ray diffraction (XRD) analysis, and are shown in FIG. 5.

As in comparative example 1 and comparative example 2, it is possible to confirm that an α-TCP phase changes into a calcium-deficient hydroxyapatites (CDHA) phase in example 1 and example 2. Thus, it may be known that cementation occurs well in example 1 and example 2 as well.

In addition, microstructures of example 1 and example 2 were confirmed through a scanning electron microscope (SEM).

Figure 6B:
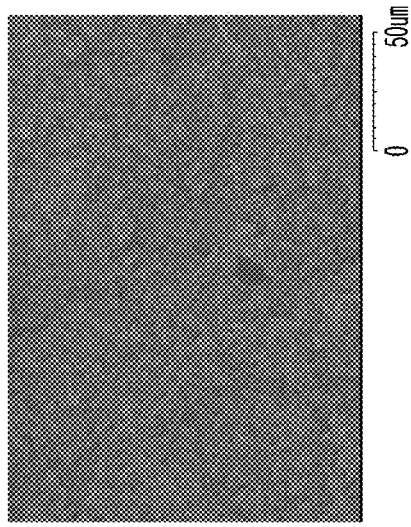
FIG. 6A and FIG. 6B show SEM images of a structure according to an example.
Figure 6A:
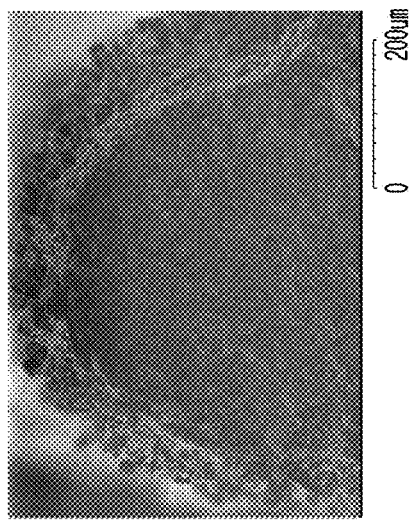

As shown in FIG. 6A and FIG. 6B, in the case of example 1, pores having a size of 1 to 3 μm are observed inside. In particular, it is possible to confirm that dicalcium phosphate dihydrate (Brushite, DCPD) is formed on the surface of a structure.

Figure 7B:
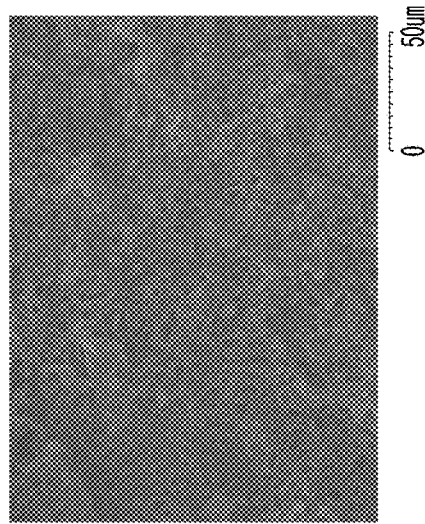
FIG. 7A and FIG. 7B show SEM images of a structure according to another example.
Figure 7A:
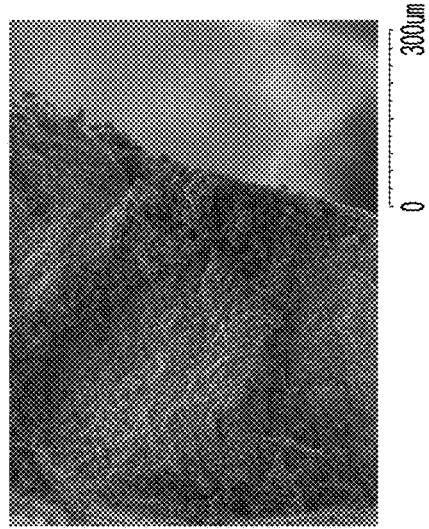

In addition, as shown in FIG. 7A and FIG. 7B, in the case of example 2, pores having a size of 8 to 10 μm are observed inside.

Figure 8B:
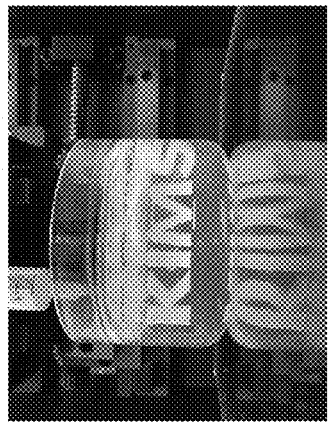
FIG. 8A shows dimensions of a ceramic 3D printing structure and FIG. 8B shows a ceramic 3D printing structure manufactured according to an example.
Figure 8A:
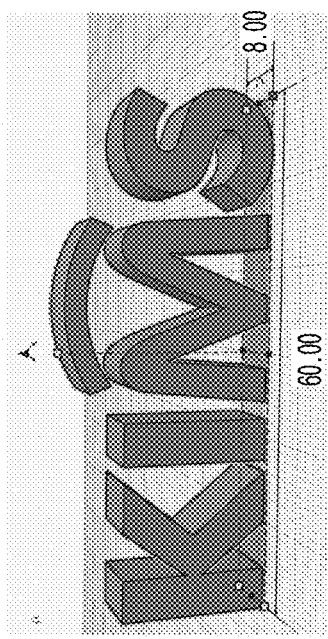

A KIMS logo having an overhang structure was manufactured by using the processes of example 1 and example 2, and is shown in FIG. 8B. A rabbit mandible requiring a large amount of supports if using an existing process was manufactured by using the processes of example 1 and example 2, and is shown in FIG. 9B and FIG. 9C.

Figure 10:
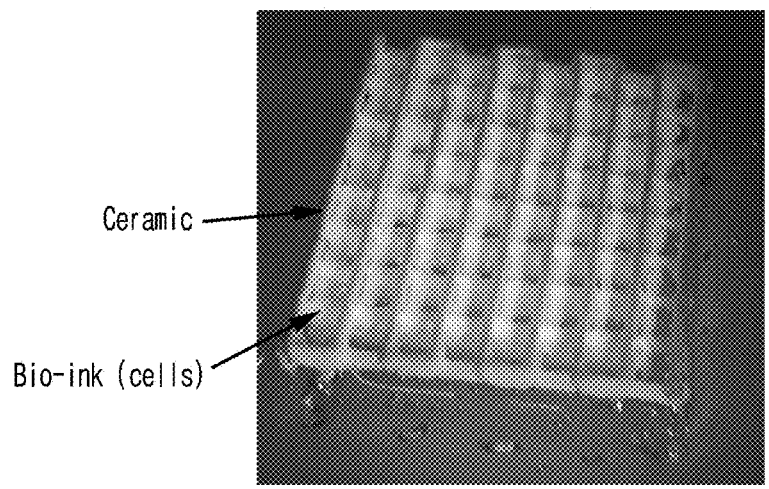
FIG. 10 shows a ceramic and biofunctional material 3D printing composite structure manufactured according to still another example.

In addition, a ceramic structure in which cells are located was manufactured by using the processes of example 1 and example 2 and printing both ceramic and bio-ink, and is shown in FIG. 10. In the case of FIG. 10, manufacturing is performed via a procedure of printing cells inside a hydrogel, and thus a wet environment is provided during a process. Therefore, high cell viability is expected.

That is, the processes of example 1 and example 2 secure the same properties as those of a support produced via an existing process, and do not require production of a separate support, and thus it is possible to overcome disadvantages of support production.

EXAMPLE 3

Evaluation on Resolutions in Accordance with Printing Conditions

With respect to example 1 and example 2, printing resolutions inside a hydrogel tank was tested while varying a nozzle size and a printing speed.

21 G, 23 G, and 25 G nozzles were used, and a printing speed varied to 400 mm/min, 500 mm/min, 600 mm/min, and 700 mm/min (FIG. 11A, FIG. 11B, and FIG. 11C, and FIG. 12A, FIG. 12B, and FIG. 12C).

Figure 11A:
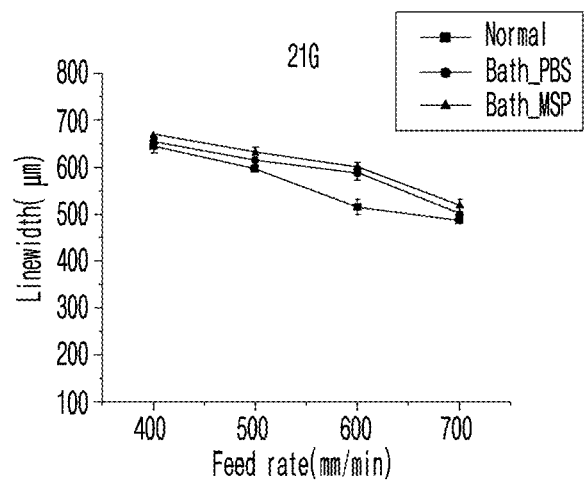
FIG. 11A, FIG. 11B, and FIG. 11C show graphs of nozzle size-specific resolutions depending on a printing speed, according to an experimental example.
Figure 11B:
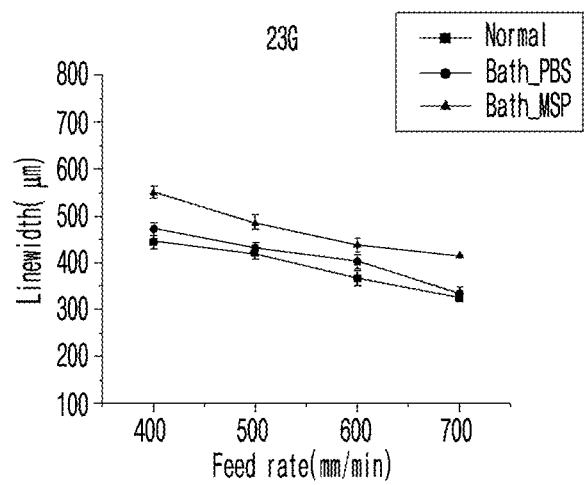
Figure 11C:
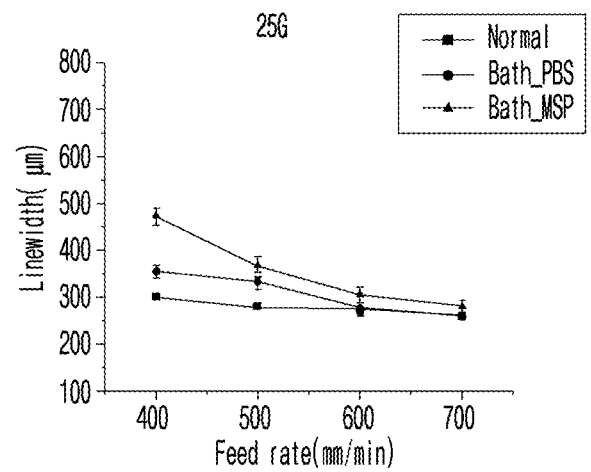
Figure 13:
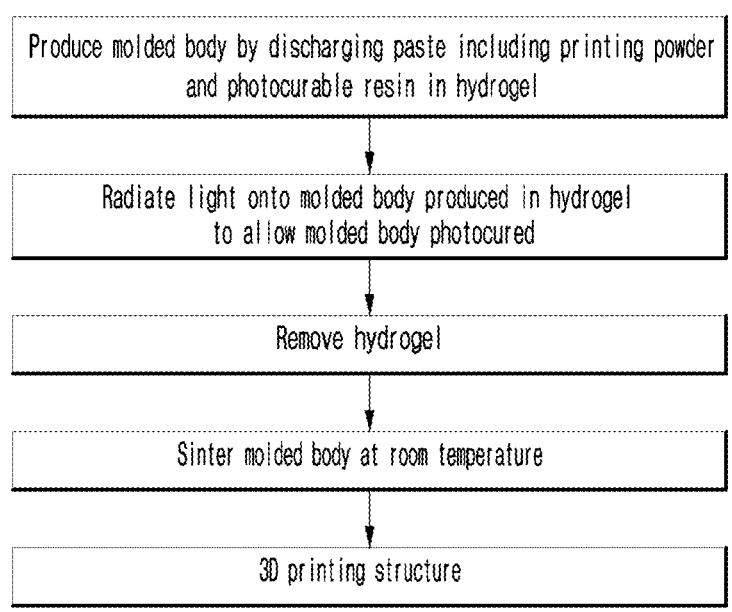
FIG. 13 is a flowchart typically showing a method for manufacturing a 3D printing structure according to another example.

In FIG. 11A, FIG. 11B, and FIG. 11C, nozzle size-specific resolutions (the linewidth of a strut) depending on a printing speed are shown. A decrease in the linewidth of a strut means enhancement in exquisiteness. As a nozzle size decreases and a printing speed increases, the linewidth decreases, and it is possible to confirm that printing becomes more exquisite.

In addition, in the case of comparative example 1, resolutions are 260 μm to 645 μm. In the case of example 1 and example 2, resolutions are 260 μm to 660 μm and 280 μm to 670 μm, respectively. Thus, it may be known that resolutions which are almost similar to those in an existing process of not using a hydrogel are secured in example 1 and example 2.

EXAMPLE 3

3D Printing Structure Printing 3

A hydrogel was prepared by adding 10 to 30 wt % of Pluronic™ F-127 (PF-127) to distilled water.

PEFDA was used as a photocurable polymer in ink, and 45 vol % of alumina, 45 vol % zirconia, 45 vol % titania, 55 vol % bioglass, 40 vol % of stainless steel, and 50 vol % of $Ti_6Al_4V$ were added to printing powder in the ink.

Paste was put into an extrusion container, and a three-dimensional structure was molded in a hydrogel tank by using a 3D printer. A support molded in the hydrogel tank was hardened by radiating UV thereonto.

Thereafter, the temperature of the hydrogel was adjusted to about 20° C. or less, and the hydrogel was exposed for 20 minutes, so that the hydrogel was solated. The hydrogel accordingly converted into an aqueous solution state was removed, and a molded body was washed.

A sintered body was produced by sintering the molded body at a high temperature.

Figure 14:
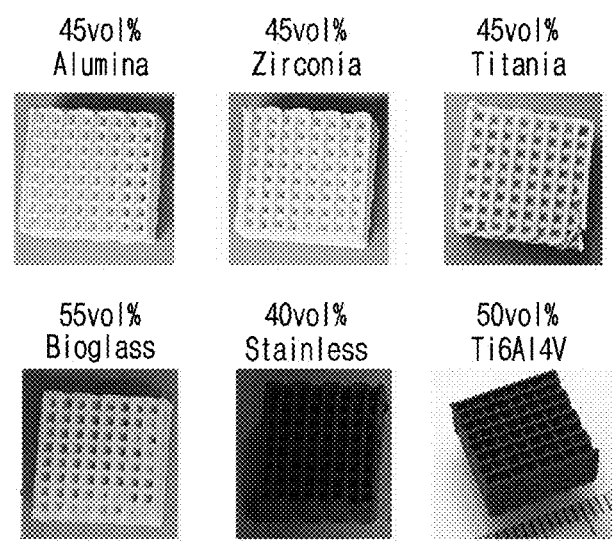
FIG. 14 shows 3D printing structures, which are printed with various materials, manufactured according to another example.

Result products therefrom are shown in FIG. 14, and it is possible to confirm that a three-dimensional structure is successfully formed by each of all ceramic and metal materials.

EXAMPLE 4

Evaluation on Resolutions in Accordance with Printing Conditions

With respect to the inclusion of alumina powder in ink in example 3, printing resolutions in a hydrogel tank were tested while varying a nozzle size, a printing speed, and a discharge pressure level.

Figure 15:
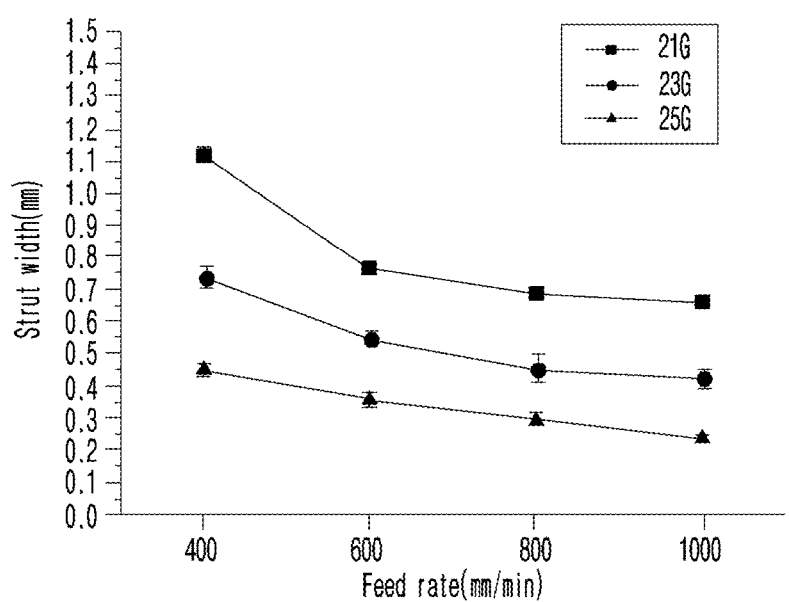
FIG. 15 is a graph showing nozzle size-specific resolutions depending on a printing speed under discharge pressure levels different from each other, according to an experimental example.
Figure 16:
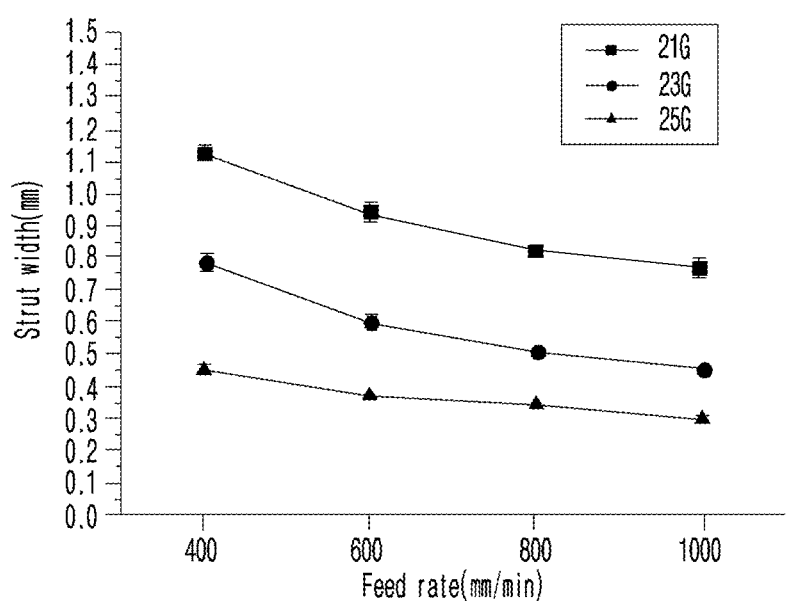
FIG. 16 is a graph showing nozzle size-specific resolutions depending on a printing speed under discharge pressure levels different from each other, according to an experimental example.

A case in which a discharge pressure level is 380 kPa is shown in FIG. 15, and a case in which a discharge pressure level is 400 kPa is shown in FIG. 16. In each of FIG. 15 and FIG. 16, 21 G, 23 G, and 25 G nozzles were used, and a printing speed varied to 400 mm/min, 600 mm/min, 800 mm/min, and 1000 mm/min.

In each of FIG. 15 and FIG. 16, nozzle size-specific resolutions (the linewidth of a strut) depending on a printing speed are shown. The resolutions are confirmed to be 200 μm to 1100 μm.

A decrease in the linewidth of a strut means enhancement in exquisiteness. As a nozzle size decreases and a printing speed increases, the linewidth decreases, and it is possible to confirm that printing becomes more exquisite.

In addition, comparing FIG. 15 and FIG. 16, it is possible to confirm that printing becomes more exquisite due to a decrease in a configured strut linewidth if a discharge pressure level is low.

What is claimed is:

1. A method for manufacturing a 3D printing structure, the method comprising: producing a molded body by performing 3D printing on paste including printing powder in a coagulation bath including a hydrogel; hardening the molded body produced in the coagulation bath; and removing the hydrogel in the coagulation bath; and completely hardening the molded body after the removing of the hydrogel in the coagulation bath, wherein the completely hardening of the molded body is performed at a temperature of 20° C. to 60° C.

2. The method of claim 1, wherein the coagulation bath further includes a hardening agent.

3. The method of claim 1, wherein the paste includes a thickening agent.

4. The method of claim 1, wherein the paste includes one or more alcohols selected from the group consisting of methanol, ethanol, propanol, and butanol.

5. The method of claim 1, wherein the hardening of the molded body produced in the coagulation bath is performed at a temperature of 20° C. to 70° C. for 30 minutes or more.

6. The method of claim 1, wherein the 3D printing structure at least partially includes an overhang structure.

7. The method of claim 1, wherein the removing of the hydrogel in the coagulation bath includes one or more among:
solating the hydrogel and then removing the coagulation bath;
dissociating the crosslinking of the hydrogel which has been crosslinked; and
introducing the coagulation bath into a buffer and dissolving the coagulation bath.

8. The method of claim 7, wherein the solating is performed by one or more among schemes including temperature adjustment and pH adjustment.

9. The method of claim 1, wherein the hydrogel includes one or more materials selected from the group consisting of Pluronic F-127 (PF-127), gelatin, poly(N-isopropylacrylamide), agarose, carrageenan, gellan gum, xanthan gum, alginate, Carbopol, and Laponite nanoclay.

10. The method of claim 9, wherein the hydrogel includes, in a concentration of 0.1 to 40 wt %, the one or more materials selected from the group consisting of Pluronic F-127 (PF-127), gelatin, poly(N-isopropylacrylamide), agarose, carrageenan, gellan gum, xanthan gum, alginate, Carbopol, and Laponite nanoclay.

11. The method of claim 1, wherein the paste further includes cells.

12. The method of claim 11, wherein the cells are one or more selected from the group consisting of human bone marrow-derived mesenchymal stem cells, adipose-derived mesenchymal stem cells, induced pluripotent stem cells, vascular endothelial cells, osteoblasts, chondrocytes, fibroblasts, and a mixture thereof.

13. The method of claim 1, wherein the paste further includes a biofunctional material.

14. The method of claim 13, wherein the biofunctional material is one or more selected from the group consisting of a growth factor, a protein, a protein drug, an antiproliferative agent, antithrombin, an immunosuppressant, a lipid, an antilipid, a liposome, an anti-inflammatory agent, an antitumor agent, an antiplatelet agent, an angiogenic agent, an antiangiogenic agent, a vitamin, an aptamer, an antimitotic agent, a metalloproteinase inhibitor, an NO donor, estradiol, an antisclerosing agent, a vasoactive agent, a beta blocking agent, an AZ blocking agent, a hormone, statins, an antioxidant agent, a membrane stabilizer, a calcium antagonist, retinoid, a peptide, a lipoprotein, a polypeptide, a polynucleotide encoding polypeptide, an enzyme, a genetic material, a chemical solvent, an energy-activator, a lymphocyte inhibiting material, a macrophage inhibiting material, and a mixture thereof.

15. The method of claim 1, wherein the 3D printing structure is a hard tissue-regenerating support.

16. The method of claim 15, wherein when the 3D printing structure includes a plurality of layers, the performing of the 3D printing on the paste including printing powder and the hardening of the molded body by radiating light are repeated multiple times.

17. The method of claim 1, wherein the paste further includes a photocurable resin, and the hardening of the molded body produced in the coagulation bath is performed by radiating light.

18. The method of claim 17, wherein the photocurable resin includes one or more selected from the group consisting of PEGDA, HDDA, Laromer, TEGDMA, PPGDA, TMPTA, alginate-methacrylate, gelatin-methacrylate, hyaluronic acid methacrylate, and collagen-methacrylate.

* * * * *